United States Patent [19]

Sam

[11] 4,364,123
[45] Dec. 21, 1982

[54] COMBINATION SUN SHADE AND ARTICLE CARRY-ALL

[76] Inventor: Doris L. Sam, 927 Fernrest Dr., Harbor City, Calif. 90710

[21] Appl. No.: 207,207

[22] Filed: Nov. 17, 1980

[51] Int. Cl.³ .............................................. A42B 1/06
[52] U.S. Cl. ..................................................... 2/209.1
[58] Field of Search ..................... 2/206, 209.1, 177, 8

[56] References Cited

U.S. PATENT DOCUMENTS 3,114,914 12/1963 Ruggiero ..................................... 2/8
3,651,847 3/1972 Casamassima .......................... 2/177
4,121,303 10/1978 Reece ....................................... 2/206

*Primary Examiner*—Doris L. Troutman
*Attorney, Agent, or Firm*—Sellers and Brace

[57] ABSTRACT

A versatile sunbathing accessory selectively usable as a carry-all for personal items while en route to and from the beach or park and as a sun shade for the head while enjoying sunbathing.

The accessory has a one-piece scoop-like main body and a pair of carrying handles which optionally pivot to a retracted position against the main body while the accessory is functioning as a sunshade.

5 Claims, 3 Drawing Figures

COMBINATION SUN SHADE AND ARTICLE CARRY-ALL

This invention relates to an improved sunbathing accessory, and more particularly to a novel combination sunshade and carry-all for personal items.

BACKGROUND OF THE INVENTION

Various proposals have been made heretofore for sunshades and particularly various types of head gear specially designed and proportioned to shield the user's head from sunrays while at the beach or enjoying sunbathing. Typical prior designs intended for such purposes are shown in the U.S. Patent to Halstead No. 567,234; Wittcoff No. 2,147,872; Gallowhur No. 2,391,059; Robinson No. 3,245,083; Casamassima No. 3,651,847; and Hovhannessian No. 4,157,592. However, these prior designs are subject to various shortcomings and disadvantages avoided by my invention. These include unnecessary complexity, numerous parts requiring a series of assembly operations, excessive weight and bulk and, for the most part, lack of provision for any other purpose and particularly provision for stowing and transporting personal items and articles useful for personal convenience while away from home on an outing to enjoy the sun.

SUMMARY OF THE INVENTION

This invention avoids the shortcomings and disadvantages of prior related proposals and provides a simple light-weight inexpensive article of manufacture selectively useful as a carry-all for articles of apparel, towels and other personal items customarily used by sunbathers and additionally as a sunshade for the head. The sunshade is generally scoop shaped and designed to be readily supported at a desired inclination while pressed against a supporting surface by the user's head. A pair of carrying handles pivoted to the main body are readily folded to a retracted position against the main body when not in use for carrying purposes.

The main body is preferably made in one piece from molded plastic material and the carrying handles may be secured to the rim of the opening by snap fasteners or the like.

These and other more specific objects will appear upon reading the following specification and claims and upon considering in connection therewith the attached drawing to which they relate.

Referring now to the drawing in which a preferred embodiment of the invention is illustrated:

Figure 1:
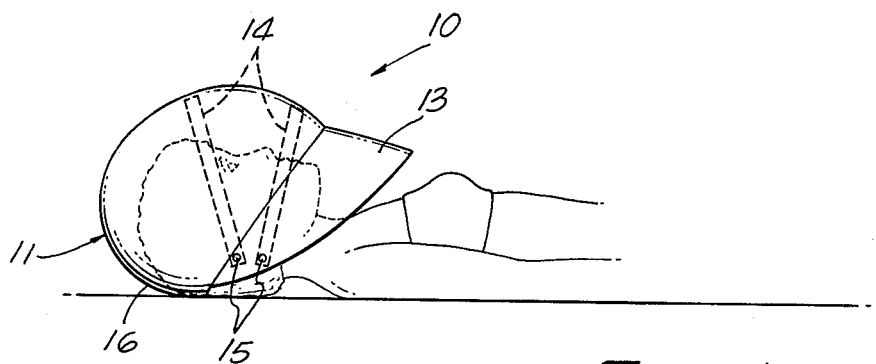
FIG. 1 is a side elevational view of an illustrative embodiment of the invention accessory while in use as a sun shade.
Figure 2:
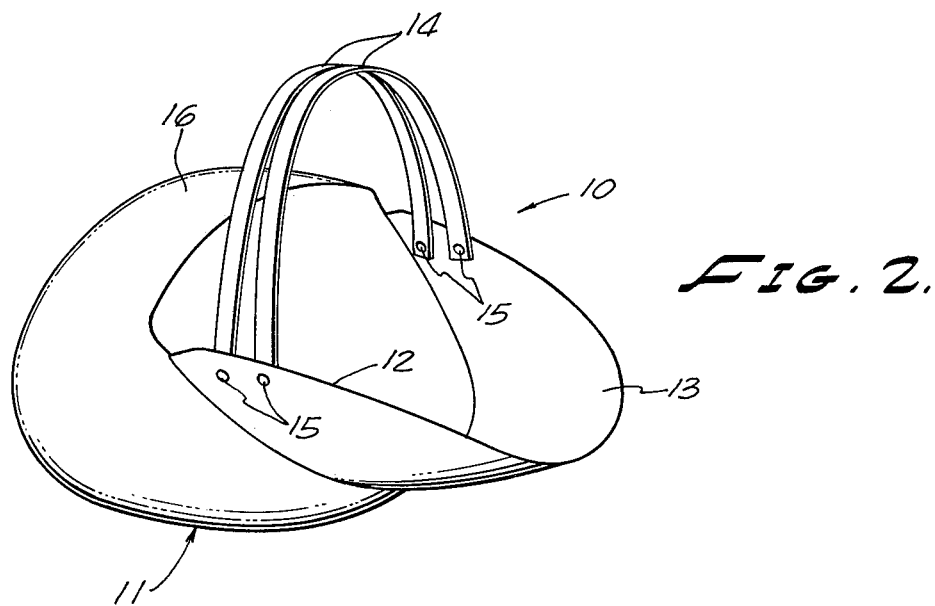
FIG. 2 is a perspective view of the accessory with the carrying handles extended and the sunshade exposed for use to receive personal items.

Referring more particularly to FIG. 2, there is shown a combination sunshade and carry-all designated generally 10. The accessory has a scoop-like main body 11 here shown as molded in one piece from suitable essentially opaque plastic material. For example, the accessory may be blow molded or vacuum molded in a manner well known to those skilled in the plastic molding art. As shown in finished form, the accessory has a relatively large opening receiving the user's head and coiffeur with ample additional air space thereabout for ventilation and breathing. When removed from the mold, the inlet opening may be and usually is substantially smaller but this opening is readily trimmed and enlarged to form the elongated oval opening 12 indicated in the several views. The principal part of the accessory is generally dome shaped and provided along one rim edge with an extensive integral canopy or visor 13 shaped to shield the neck and upper portion of the torso in the manner shown in FIG. 1.

Figure 3:
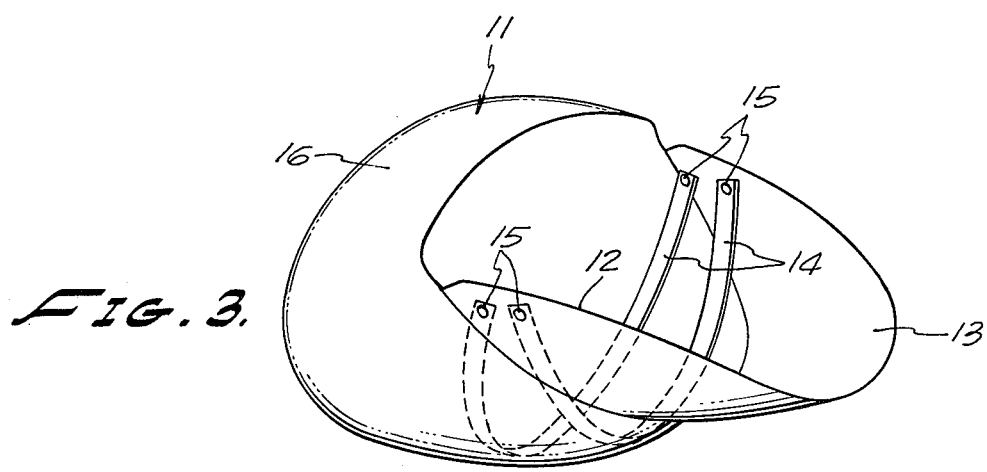
FIG. 3 is a view similar to FIG. 2 but showing the carrying handles pivoted to a retracted position against the surface of the sunshade.

Pivoted to the opposite sides of visor 13 are a pair of carrying handles 14, 14. As here shown, these pivots comprise snap fasteners making it a simple matter to assemble the handles to the accessory as well as to detach them when not in use as a carrier if the user so prefers. Desirably, handles 14 are proportioned to bear frictionally against the surface of the main body when in the retracted position shown in FIGS. 1 and 3. Thus these handles have an interference fit with the surface of the main body so that they remain firmly retracted until and unless forceably pivoted to their extended position.

The rear of the main body is relatively wide and only slightly curved. This portion receives the back of the user's head when in an inclined position so that the head holds the shade firmly pressed against the ground or other supporting surface. The shade may be tilted forwardly so that visor 13 is relatively closely spaced from the neck and torso, or, if desired, is readily tilted so that the visor is inclined upwardly to permit the user to view the surrounding area and converse more readily with friends.

When not in use, handles 14 are pivoted to the position shown in FIG. 1 and used to store towels, lotions and other personal items customarily used by sunbathers.

While the particular combination sun shade and article carry-all herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. A sun bathing accessory having an elongated scoop-like main body of opaque plastic material shaped and sized to accommodate and shade the head of a sunbather, said main body having a cup-shaped chamber at the rear end thereof substantially larger than the user's head and coiffeur and provided with a canopy at its forward end adapted to overlie and shade the user's face and neck, and carrying handle means extending crosswise of the midlength of said main body for use in stowing and carrying said accessory and personal articles placed therein when said accessory is not in use as a sunshade.

2. A sunbathing accessory as defined in claim 1 characterized in that said main body is formed in one piece of flexible plastic material.

3. A sun bathing accessory as defined in claim 2 characterized in that said handle means includes a pair of straps having means at the opposite ends thereof connected to spaced apart points along the opposite lateral sides of said main body.

4. A sun bathing accessory as defined in claim 3 characterized in that at least one end of said pair of straps is detachable from said main body.

5. A sun bathing accessory as defined in claim 1 characterized in that the portion of the side wall of said cup-shaped rear end diametrically opposite said canopy is adapted to be pressed against an underlying support when the user's head is resting against the interior of said rear end and thereby effective to hold said sunshade firmly supported in a desired sun shading position relative to the user's head.

* * * * *